(12) United States Patent
Roschak et al.

(10) Patent No.: US 8,235,908 B2
(45) Date of Patent: Aug. 7, 2012

(54) BLOOD VESSEL SENSING CATHETER HAVING WORKING LUMEN FOR MEDICAL APPLIANCES

(75) Inventors: Edmund J. Roschak, Mission Viejo, CA (US); Thomas M. Keast, Sunnyvale, CA (US); Eric J. Gwerder, Fremont, CA (US)

(73) Assignee: Broncus Medical, Mountain View, CA (US)

( * ) Notice: Subject to any disclaimer, the term of this patent is extended or adjusted under 35 U.S.C. 154(b) by 438 days.

(21) Appl. No.: 12/406,018

(22) Filed: Mar. 17, 2009

(65) Prior Publication Data

US 2009/0275840 A1 Nov. 5, 2009

Related U.S. Application Data

(63) Continuation of application No. PCT/US2008/056069, filed on Mar. 6, 2008.

(60) Provisional application No. 60/893,174, filed on Mar. 6, 2007.

(51) Int. Cl.
*A61B 8/00* (2006.01)

(52) U.S. Cl. ........ 600/453; 600/466; 600/471; 600/529; 600/104

(58) Field of Classification Search .......... 600/407, 600/453, 466, 465, 104, 529, 471, 438
See application file for complete search history.

(56) References Cited

U.S. PATENT DOCUMENTS

| | | | |
|---|---|---|---|
| 6,306,096 B1 | 10/2001 | Seward et al. | |
| 6,516,213 B1 | 2/2003 | Nevo | |
| 6,551,302 B1 | 4/2003 | Rosinko et al. | |
| 6,692,494 B1 | 2/2004 | Cooper et al. | |
| 6,712,812 B2 | 3/2004 | Roschak et al. | |
| 6,749,606 B2 | 6/2004 | Keast et al. | |
| 6,770,070 B1 | 8/2004 | Balbierz | |
| 7,175,644 B2 | 2/2007 | Cooper et al. | |
| 2002/0128647 A1 | 9/2002 | Roschak et al. | |
| 2002/0138074 A1 | 9/2002 | Keast et al. | |
| 2003/0070676 A1 | 4/2003 | Cooper et al. | |
| 2003/0130657 A1 | 7/2003 | Tom et al. | |
| 2004/0220556 A1* | 11/2004 | Cooper et al. | 606/1 |
| 2005/0107783 A1 | 5/2005 | Tom et al. | |
| 2005/0165342 A1 | 7/2005 | Odland | |
| 2005/0288549 A1* | 12/2005 | Mathis | 600/104 |
| 2006/0135984 A1 | 6/2006 | Kramer et al. | |
| 2006/0183973 A1* | 8/2006 | Kamrava | 600/105 |
| 2007/0255304 A1 | 11/2007 | Roschak et al. | |

* cited by examiner

*Primary Examiner* — Brian Casler
*Assistant Examiner* — Amanda Lauritzen
(74) *Attorney, Agent, or Firm* — Levine Bagade Han LLP

(57) ABSTRACT

Devices and methods are disclosed for providing a sensing element to scan tissue and detect the presence of structures within the tissue to avoid the structures when performing a procedure on the tissue. A catheter includes a blood vessel sensing assembly and a working lumen adapted to receive a medical appliance or instrument for performing various medical procedures.

6 Claims, 8 Drawing Sheets

BLOOD VESSEL SENSING CATHETER HAVING WORKING LUMEN FOR MEDICAL APPLIANCES

CROSS-REFERENCE TO RELATED APPLICATIONS

This application is a continuation of International Application No. PCT/US2008/056069, filed Mar. 6, 2008 which claims priority to U.S. Provisional Application No. 60/893,174, filed Mar. 6, 2007; both applications are incorporated herein by reference in their entireties.

FIELD OF THE INVENTION

The invention is directed to devices for sensing movement within tissue at a target site to scan for the presence or absence of structures such as blood vessels so that a procedure may be performed at the target site in a safe manner.

BACKGROUND OF THE INVENTION

When performing procedures through an endoscope, bronchoscope, or other such device there is a risk that the procedure might disrupt structures beneath a tissue surface (such as blood vessels), where the disruption then causes significant complications.

One such area is within the airways of the lungs where puncturing of a blood vessel beneath the airway surface can result in significant bleeding. In cases where a scope type device is used, the bleeding obstructs the ability of the medical practitioner to visualize the damaged area resulting in an escalation of complications. In some cases, a patient's chest must be opened to stem the bleeding.

Such risks occur in many types of scope-based procedures, including but not limited to lung based approaches. For example, creation of collateral channels in COPD patients poses such risks. For example see U.S. Pat. No. 6,692,494; U.S. patent application Ser. Nos. 09/947,144, 09/946,706, and 09/947,126 all filed on Sep. 4, 2001; U.S. patent application Ser. No. 10/235,240, filed on Sep. 4, 2002; U.S. patent application Ser. No. 11/335,263, filed on Jan. 18, 2006; and U.S. patent application Ser. No. 11/562,947, filed on Nov. 22, 2006; each of which is incorporated by reference herein in its entirety. In addition, biopsy procedures, transbronchial aspiration procedures, and/or the use of cytology brushes are a few procedures that present the same risk of penetrating a blood vessel within the lungs.

The problem is further compounded when accounting for motion of the tissue. For example, because airway or other lung tissue moves due to tidal motion of the lungs (as a result of the mechanics of breathing), it is difficult to visually identify an area that was previously scanned unless the scanning device remains relatively stationary against the tissue. Moreover, the difficulty increases when considering that the procedure takes place through the camera of a bronchoscope or endoscope.

Aside from the risk to the patient, a medical practitioners that causes puncturing of a blood vessel is often understandably hesitant or risk adverse when performing future procedures. As a result, while the benefit of these procedures is well known, the risks of complications may reduce the overall success of the procedure.

In view of the above, a need remains to increase the safety when disrupting tissue beneath a tissue surface where the disruption could cause complications on structures hidden beneath the tissue surface Such a need remains in procedures that create channels to vent trapped gasses within the lungs, transbronchial aspiration procedures, transesophageal procedures, biopsy procedures, use of cytology brushes, etc. Furthermore, the need may arise in any lung based procedure or other procedures in other parts of the body.

SUMMARY OF THE INVENTION

The invention relates to devices and method for sensing structures within tissue (such as blood vessels or other organs) while performing a procedure at the site.

The catheter member can be a tubular member as commonly used in medical device applications. Accordingly, the catheter member can be a polymeric tube or a reinforced polymeric tube. As described herein, it may have one or more lumens to accommodate the variations of the devices within this disclosure.

The sensing assembly is used to scan the tissue to minimize causing undesirable injury to the patient. As discussed below, any number of sensing modes may be incorporated into the device. However, it was found that Doppler ultrasound transducer assemblies perform acceptably when sensing for blood vessels within tissue. In certain variations, the sensing assembly may be configured to puncture the tissue and create the opening. However, in other variations, the sensing assembly will have a blunted tip to minimize undesirable tissue damage.

In variations of the device, the sensing assembly is offset from an axis of the catheter assembly. Doing so improves the ability of the sensing assembly to contact tissue surfaces when the device is advanced along body conduits. In addition, this offset feature improves the ability to see the tip of the sensing assembly when the device is used with a scope type device.

The invention further includes methods of treating tissue, where the method includes selecting an area in the tissue for treatment, advancing a device into the lung to a tissue site, where the device includes a sensing assembly affixed to a catheter to sense for the presence or absence of blood vessels. The device may then allow for the use of a medical appliance such as an aspiration needle, a transbronchial aspiration needle, a forceps, a coring device, a cytology brush, etc, to perform a procedure at the site without removing the sensing assembly from the tissue site.

As noted herein, one variation of the device permits scanning the tissue site by placing the sensing assembly in contact with the tissue site. However, various sensing assemblies may permit non-contact scanning. Regardless of whether the sensing tip contacts the tissue, creation of the opening may be performed without significant movement of the scanning assembly. Such a benefit is apparent as medical practitioners may lose track of the scanned tissue if they are required to substitute or move the scanning assembly to create an opening.

DETAILED DESCRIPTION OF THE INVENTION

Figure 1A:
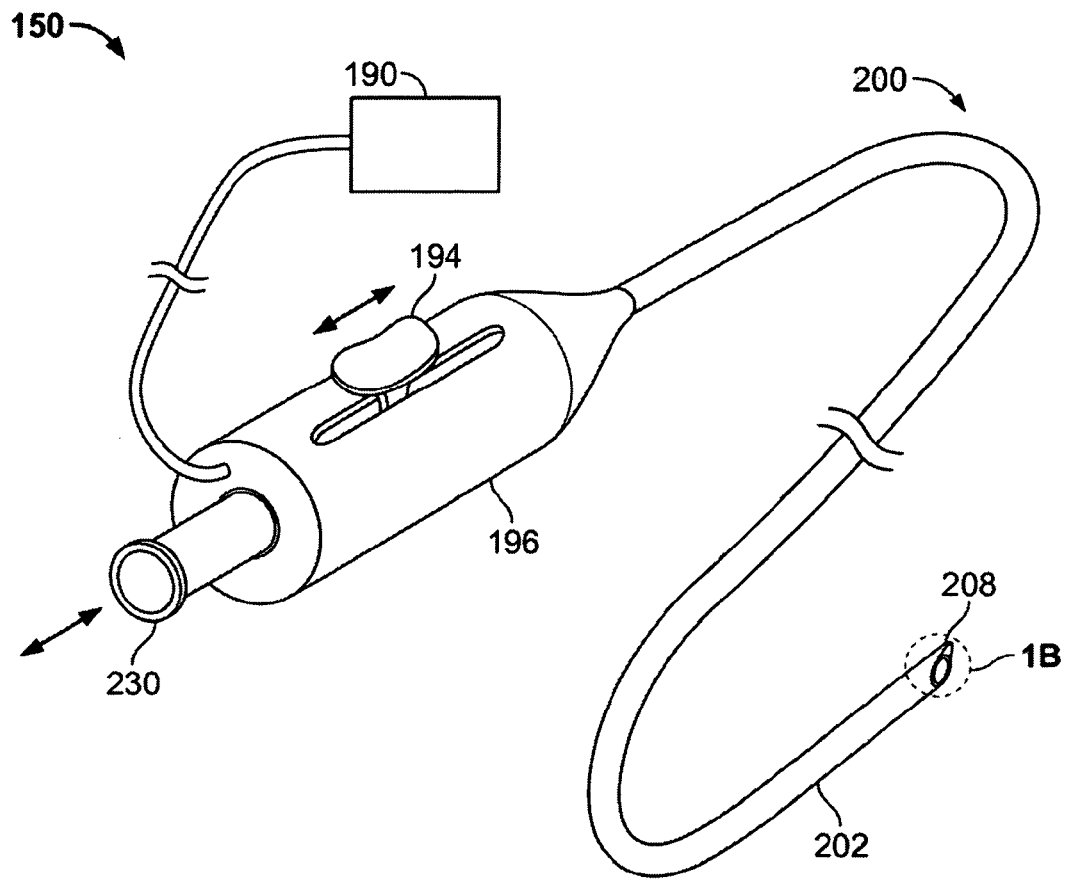
FIG. 1A shows a variation of a system as described herein.

FIG. 1A illustrates a view of a variation of the inventive system 150. The system generally includes a device 200 having a sensing element 208 located at a distal tip 203 of a catheter member 202. In the variation shown, the distal tip 203 protrudes from a distal portion of the catheter member 202.

The catheter member 202 may be a single or multi-lumen tube. However, in most variations, the catheter member 202 is sufficiently long and flexible so that the distal end of the device 200 can access remote areas within tortuous anatomy (such as the lungs).

Figure 1B:
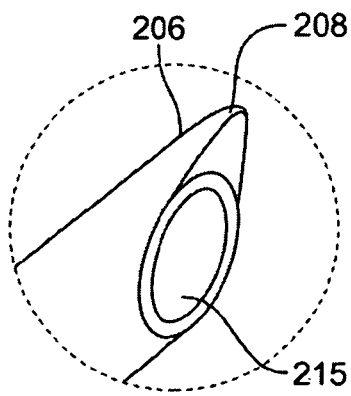
FIG. 1B shows a far end of a catheter according to the present invention.

FIG. 1B illustrates a magnified view of the distal end of the device 200 of FIG. 1A. As shown, a lumen 215 running through the catheter member 202, exits the catheter at an opening that is spaced proximally from the distal tip 203.

As shown in FIG. 1A, the device 200 also includes a handle portion 196. Typically, the handle portion 196 may be of any known handle type configuration commonly used with medical devices. However, in some variations of the device, the handle portion 196 allows manipulation of the device 200. When the device 200 is used with another medical appliance (as noted below) then handle 200 can either engage the appliance (e.g., by coupling with the appliance) or provides a surface for manipulation of the appliance relative to the device 200. Typically, the handle includes a fitting, flange, threaded portion, female luer, or other connection 230 for coupling various medical appliances. Such medical appliances include aspiration needles, transbronchial aspiration needles, biopsy devices, brushes, forceps, and other such devices that could be advanced through the lumen of the catheter 202 to the target site at the end of the device 200. In most variations, such medical appliances are of a small diameter. The use of the connector 230 provides a more convenient opening for insertion of a small device. For instance, attempting to insert an aspiration needle (e.g., 17-21 gauge) into a small diameter lumen will be a time consuming effort. Use of a connector 230 permits the medical practitioner to rapidly insert such a small sized appliance into the device 200.

The handle 196 may optionally include a sliding mechanism or actuator 194 that can be coupled to the medical appliance that is advanced through the port or connection 230. This coupling permits the medical practitioner to advance or retract the medical appliance with a single hand that is already manipulating the device 200.

In one variation, the device 200 may be coupled to a control system 190 that is configured to assist the medical practitioner in detecting whether blood vessels are at or near a particular target site. The sensing assembly 206 and control system 190 may be any type of unit that confirms the presence or absence of blood vessels. As such, it may be a thermal based system (incorporating a temperature detecting element, thermocouple, RTD, etc.), light based system (incorporating a fiber-optic system to measure reflected light or energy), ultrasound based system, or Doppler based system. The sensing element may provide an image or may simply provide sound or other data. The system 150 may also include various other components as required (e.g., fluid sources, medications, vacuum sources for aspiration, etc.)

For exemplary purposes, the control system 190 and sensing assembly 206 are discussed herein as being a Doppler ultrasound system. As such, the sensing assembly 206 includes a sensing tip 208 that is coupled to the power supply 190 as is known by those familiar with such systems. For example, the sensing assembly 206 may include any number of conducting members (e.g., wires) extending along the catheter member 202 (either internally or externally to the catheter member 202). In any case, these conducting members provide the energy and controls for the sensing assembly 206. In the case of Doppler ultrasound, the conducting members couple an ultrasound source 190 to the sensing tip 208 that comprises an ultrasound transducer assembly or lens.

Moreover, variations of the inventive device include conducting members that comprise a series of wires, with one set of wires being coupled to respective poles of the transducer, and any number of additional sets of wires extending through the device. In addition, the sensing assembly 206 may have more than one sensing surface disposed along the portion of the sensing assembly 206 that extend from the device.

As discussed herein, any conventional sensing type probe may be used to detect the blood vessel. When using Doppler ultrasound to detect the presence of blood vessels within tissue, the ultrasound can operate at any frequency in the ultrasound range but preferably between 2 Mhz-30 Mhz. It is generally known that higher frequencies provide better resolution while lower frequencies offer better penetration of tissue. In the present invention, because location of blood vessels does not require actual imaging, there may be a balance obtained between the need for resolution and for penetration of tissue. Accordingly, an intermediate frequency may be used (e.g., around 8 Mhz). A variation of the invention may include inserting a fluid or gel into the airway to provide a medium for the Doppler sensors to couple to the tissue to detect blood vessels. In those cases where fluid is not inserted, the device may use mucus found within the airway to directly couple the sensor to the wall of the airway.

As noted above, Doppler ultrasound was found to be an efficient way to identify blood vessels. As such, the control system 190 can be configured to communicate with an analyzing device or control unit adapted to recognize the reflected signal or measure the Doppler shift between the signals. The source signal may be reflected by changes in density between tissues. In such a case, the reflected signal will have the same frequency as the transmitted signal. When the source signal is reflected from blood moving within a vessel, the reflected signal has a different frequency than that of the source signal. This Doppler Effect permits determination of the presence or absence of a blood vessel within tissue. The Doppler system described herein comprises a Doppler ultrasound mode of detection. However, additional variations include transducer assemblies that allows for the observation of the Doppler Effect via light or sound as well.

Regardless of the mode incorporated by the sensing assembly, the system 150 may include a user interface that allows the user to determine the presence or absence of a blood vessel at the target site. Typically, the user interface provides an audible confirmation signal. However, the confirmation signal may be manifested in a variety of ways (e.g., light, graphically via a monitor/computer, etc.)

Although depicted as being external to the device, it is contemplated that the control system 190 may alternatively be incorporated into the device 200. Moreover, the system 150 may incorporate any number of connectors or fitting that allow for either permanent or detachable connections of the fluid source, control system and/or any other auxiliary systems used with the system 150.

Figure 2A:
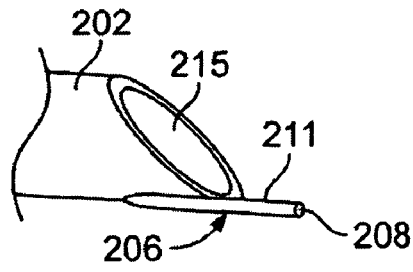
FIGS. 2A-2F show variations of the ends of devices.
Figure 2B:
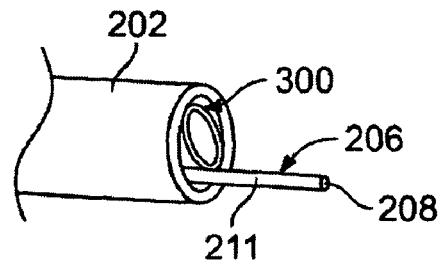

FIGS. 2A to 2B illustrate various configurations of the far end of the catheter member 202 to illustrate variations of sensing assembly 206 configurations relative to the opening of the lumen 215. As noted, the device may include any number of lumens.

FIG. 2A shows a variation of a sensing element 208 having a segment 211 that extends from the tip of the catheter 202 and where the opening of the lumen 215 is tapered. As discussed herein, in most variations, the sensing tip 208 is fixed and extends a distance beyond the catheter 202 so that the tip 208 may be pressed against tissue to scan for blood vessels or other structures. Once the practitioner locates an acceptable site, the practitioner advances the medical appliance to perform a procedure at the site.

FIGS. 2B-2F illustrate variations of sensing assemblies 206 in which the segments 211 are offset from a central axis of the catheter member 202. Offsetting the sensing element 208 from the opening of the lumen 215 decreases the chance that the sensing tip 208 will be obscured by the catheter member 202 when viewed by the end of the bronchoscope or endoscope.

FIG. 2B illustrates another variation of a sensing element 208 extending from the far end of a catheter member 202. In this variation, the sensing element 208 is located on an extension segment 211 that is affixed to the catheter member 202. FIG. 2B also shows a device or appliance 300 extending within the lumen 215. The segment 211 may extend through the length of the catheter member 202 or may be terminated near the far end of the catheter member 202 with the conductive elements (e.g., wires) extending to the control system (not shown). In some variations, the segment 211 extends through the device but the portion extending from the far end of the catheter is stiff/has a sufficient column strength to probe tissue while a remainder of the segment has a lower stiffness/column strength to accommodate flexibility of the device. In any such constructions, the conductive element (or segment portion that extends in the device) does not significantly reduce the ability to navigate the device through tortuous anatomy.

Figure 2C:
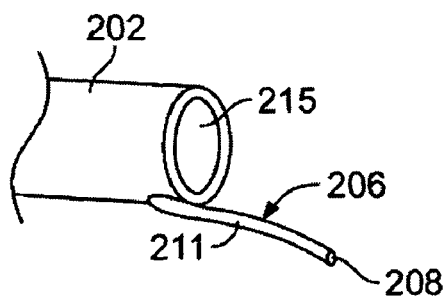

FIG. 2C illustrates another variation of a in which the sensing tip 208 is angled away from a central axis of the catheter member 202. Such a feature is useful when trying to sense along a wall of a body passage because less articulation of the catheter 202 is required to cause the sensing tip 208 to contact the tissue.

Figure 2D:
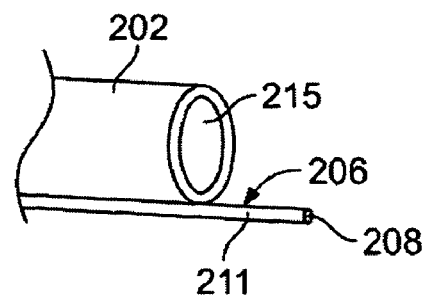

FIG. 2D shows another variation of an offset sensing assembly 206. In this variation, the segment 211 may comprise a tube or similar member that extends along and externally to the length of the catheter member 202.

Figure 2E:
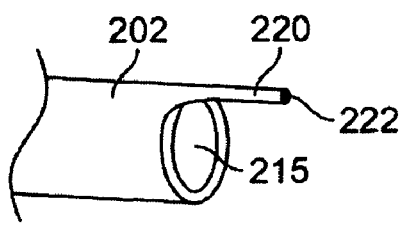

FIG. 2E illustrates yet another variation, similar to that of FIG. 2A above, where the opening of the lumen 215 is not tapered. In this variation, the catheter 202 includes a second lumen 222 through which a sensing assembly (not shown) may be secured.

Figure 2F:
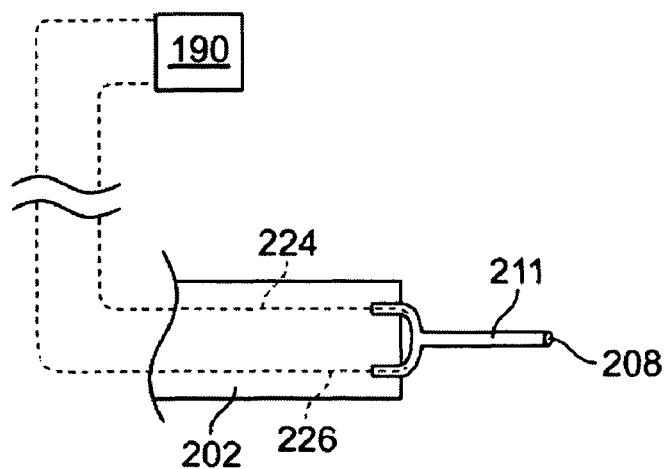

FIG. 2F shows another variation in which a segment 211 of a sensing assembly is inserted into the far end of the catheter member. The segment 211 may have connections for coupling to a control system as described above. In such a variation, the catheter member 202 may be a multi-lumen tube with one or more lumens reserved for the sensing assembly. In addition, the location of the segment 211 may be offset as described above. Alternatively, the segment 211 may be placed in the center of the catheter member 202. Given this configuration, the lumen for a dilation member such as a dilator or an expandable balloon (not shown) is offset.

The degree to which the segment 211 and sensing tip 208 extend from the catheter member 202 may vary depending on the particular application. For example, in certain variations, the sensing tip may be immediately distal to the end of the catheter member. In alternate variations, the sensing tip may extend as shown in the drawings. Such a construction is useful when the practitioner desires to insert the sensing tip 208 into an opening within the tissue to perform additional scanning.

Figure 3A:
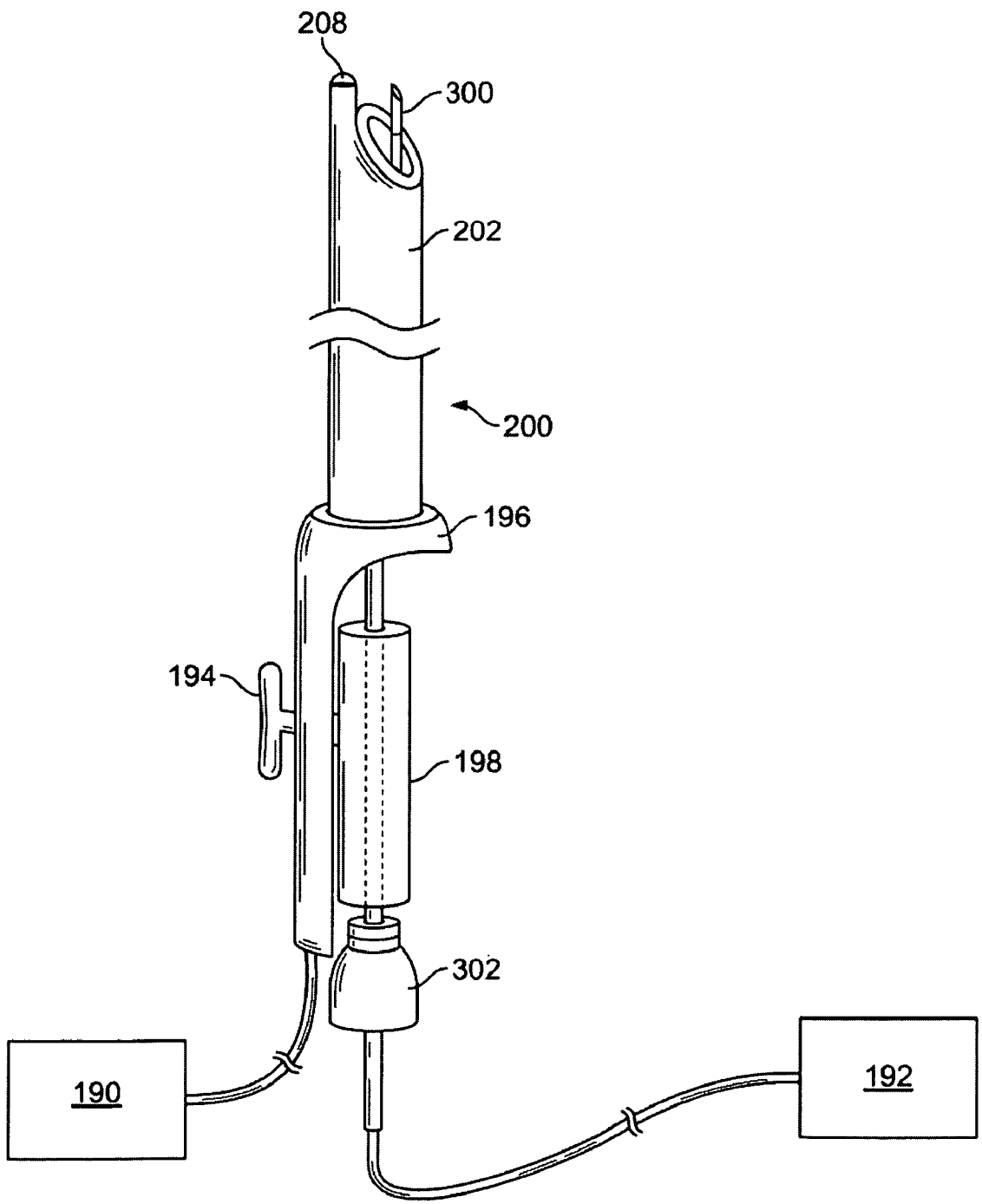
FIGS. 3A-3C show additional variations of the device.

FIG. 3A illustrates another variation of a device 200. In this variation, the device 200 includes a "partial-handle" 196 type configuration. The handle 196 includes a coupling element 198 for engaging a medical appliance 300 (in this case a trans-bronchial aspiration needle). The coupling element 198 can be manipulated by the actuator 194 on the handle 196. Optionally, the appliance 300 may include a fitting 302 such as a luer lock or hub that engages the handle 196 so that the appliance 300 may be coupled to the catheter device 200. As shown, the appliance 300 may be coupled to an auxiliary unit 192 (such as a vacuum source).

Figure 3B:
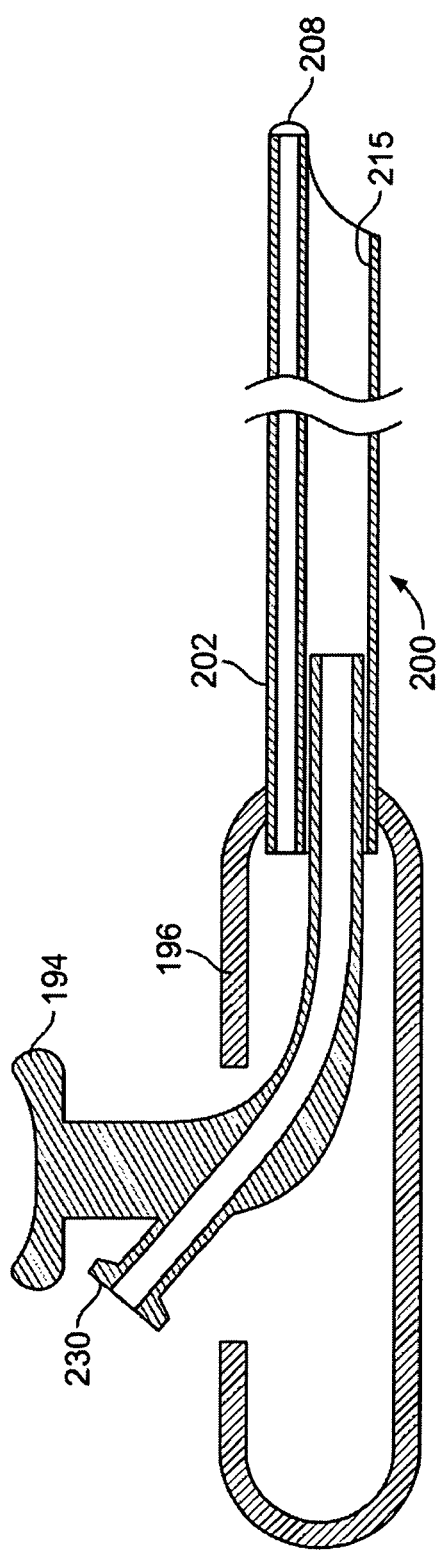
Figure 3C:
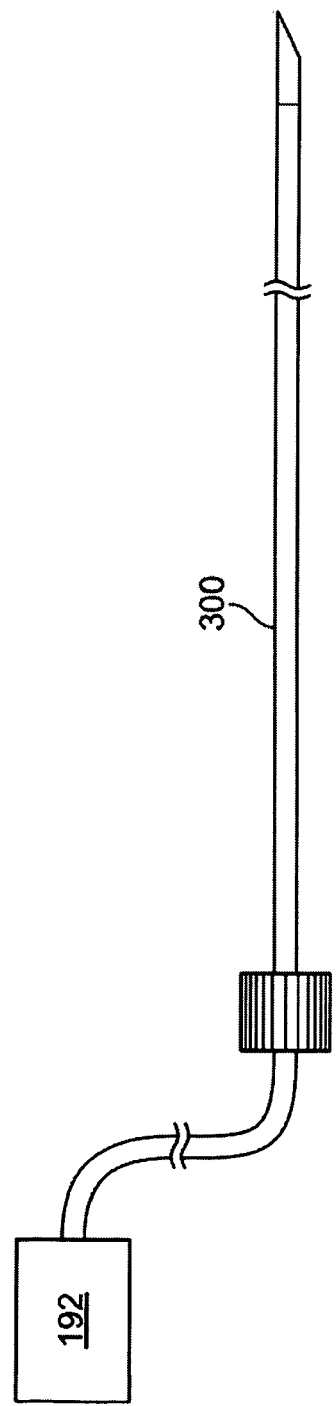

FIGS. 3B-3C illustrate another variation of a device in which the connector 230 is located to a side of the device 200 allowing for loading of the medical appliance 300 through a side of the device rather than through the proximal end. As shown, the handle 196 may also include an actuating member 194 for advancing and/or retracting the appliance 300 once inserted through the device. In an application, medical appliance 300 (e.g., a transbronchial aspiration needle) is inserted through connector 230 and advanced until hub 231 is secured to the connector. The hub and connector may be a wide variety of structures including, for example, a male and female luer connector.

Although not shown, the device lumen 215 can be configured to hold any number of medical appliances (including forceps, needles, brushes, etc.) where the appropriate device may be temporarily secured to the handle portion 196 or a coupler. Accordingly, such a variation permits the device to function as a housing for the various medical appliances.

Figure 4A:
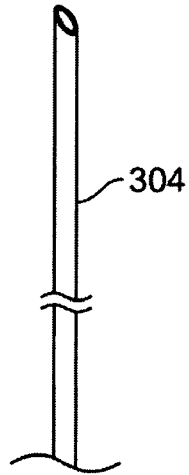
FIG. 4A-4D illustrate various medical appliances for use with the sensing device.
Figure 4B:
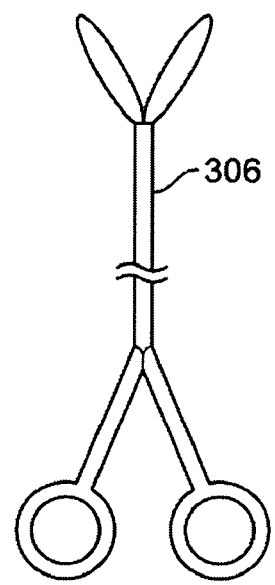
Figure 4C:
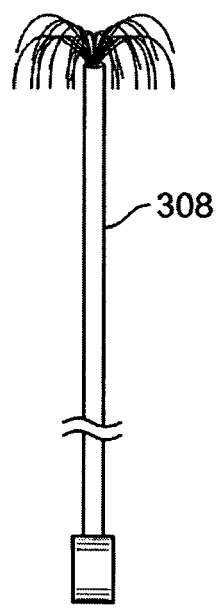
Figure 4D:
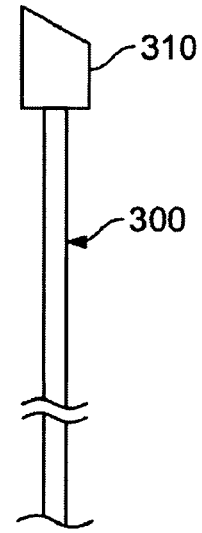

FIGS. 4A-4D illustrate some possible variations of medical appliances 300 for use in the device. As noted above, the appliance may be a simple aspiration needle 304 or a transbronchial aspiration needle. Alternatively, the appliance may be a biopsy device (e.g., a coring device) or the forceps 306 as shown in FIG. 4B. Another variation of the appliance may include a brush (e.g., a cytology brush) that obtains tissue samples when moved against the tissue site. FIG. 4D illustrates another variation of an appliance 300. In this variation, the appliance 300 includes a removable working tip 310. The working tip 310 may be interchangeable with other working tips to perform a number of functions (e.g., coring, aspiration, tissue sampling, etc.)

Figure 5A:
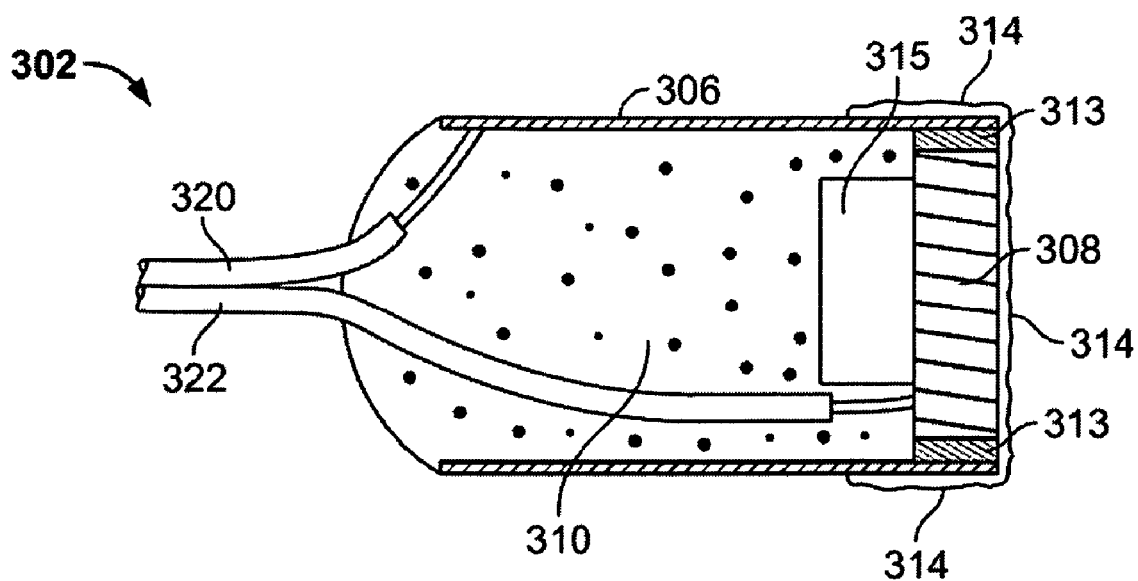
FIGS. 5A-5B illustrate a non-exhaustive sample of variations of transducer assemblies.
Figure 5B:
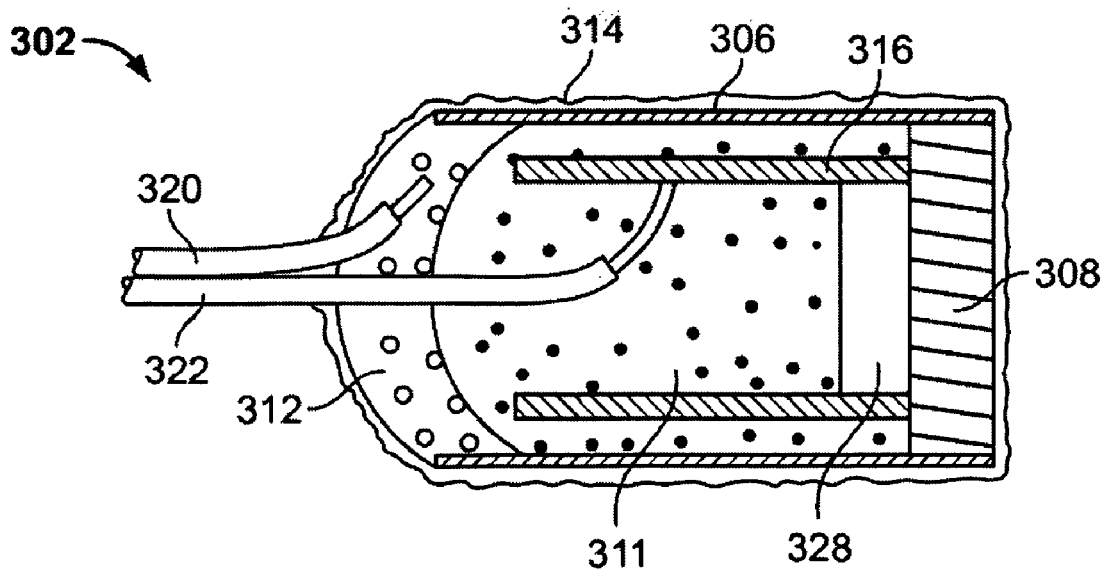

It was noted above that the sensing element 208 can include any number of sensing modes as discussed above. One such possible mode includes a transducer assembly as shown in FIGS. 5A-5B FIG. 5A illustrates a cross-sectional view of a basic variation of a transducer assembly 302. The transducer assembly 302 includes at least one transducer 308 (e.g., a piezoelectric transducer.) In this variation, the front surface of the transducer 308 comprises a first pole and the rear surface comprises a second pole.

The transducer or transducers may comprise a piezo-ceramic crystal (e.g., a Motorola PZT 3203 HD ceramic). In the current invention, a single-crystal piezo (SCP) is preferred, but the invention does not exclude the use of other types of ferroelectric material such as poly-crystalline ceramic piezos, polymer piezos, or polymer composites. The substrate, typically made from piezoelectric single crystals (SCP) or ceramics such as PZT, PLZT, PMN, PMN-PT; also, the crystal may be a multi layer composite of a ceramic piezoelectric material. Piezoelectric polymers such as PVDF may also be used. Micromachined transducers, such as those constructed on the surface of a silicon wafer are also contemplated (e.g., such as those provided by Sensant of San Leandro, Calif.) As described herein, the transducer or transducers used may be ceramic pieces coated with a conductive coating, such as gold. Other conductive coatings include sputtered metal, metals, or alloys, such as a member of the Platinum Group of the Periodic Table (Ru, Rh, Pd, Re, Os, Ir, and Pt) or gold. Titanium (Ti) is also especially suitable. The transducer may be further coated with a biocompatible layer such as Parylene or Parylene C.

The covering 306 of the transducer assembly 302 may contain at least a portion of the transducer 308. In some variations of the invention, the covering 306 may comprise a conductive material. In such cases the covering 306 itself becomes part of the electrical path to the first pole of the transducer 308. Use of a conductive covering 306 may require insulating material 313 between the sides of the transducer 308, thereby permitting a first conductive medium 314 to electrically couple only one pole of the transducer 308 to the covering 306.

At least a portion of the front surface of the transducer 308 will be in contact with the conductive medium 314. The conductive medium 314 permits one of the poles of the transducer 308 to be placed in communication with a conducting member that is ultimately coupled to a power supply. As shown in this example, the conductive medium 314 places the pole of the transducer 308 in electrical communication with the covering 306. In some variations the conductive medium 314 may coat the entire transducer 308 and covering 306. Alternatively, the conductive medium 314 may be placed over an area small enough to allow for an electrical path between a conducting member and the respective pole of the transducer 308. The conductive medium 314 may be any conductive material (e.g., gold, silver, tantalum, copper, chrome, or any bio-compatible conductive material, etc. The material may be coated, deposited, plated, painted, wound, wrapped (e.g., a conductive foil), etc. onto the transducer assembly 302.

The transducer assembly 302 depicted in FIG. 5A also illustrates conducting members 320, 322 electrically coupled to respective poles of the transducer 308. Optionally, the conducting members 320, 322 may be encapsulated within an epoxy 311 located within the covering 306. The epoxy 311 may extend to the transducer 308 thereby assisting in retaining both the conducting members 320, 322 and transducer 308 within the covering. It may also be desirable to maintain a gap 328 between the transducer 308 and any other structure. It is believed that this gap 228 improves the ability of the transducer assembly 302 to generate a signal.

FIG. 5B illustrates another variation of a transducer assembly 302. In this variation, the conductive medium 314 extends over the entire transducer covering 306. Accordingly, the covering 306 may be made of a non-conducting material (e.g., a polyamide tube, polyetherimide, polycarbonate, etc.) The transducer assembly 302 may further comprise a second tube 316 within the covering 306. This second tube 316 may be a hypo-tube and may optionally be used to electrically couple one of the conducting members to a pole of the transducer 308. As shown, the covering 306 may contain a non-conductive epoxy 310 (e.g., Hysol 2039/3561 with Scotchlite glass microspheres B23/500) which secures both the conducting member and the second tube 316 within the covering 306. This construction may have the further effect of structurally securing the transducer 308 within the assembly 302. Again, a gap 328 may or may not be adjacent to the transducer to permit displacement of the transducer 308.

FIG. 5B also illustrates the assembly 302 as having a conductive epoxy 312 which encapsulates the alternate conducting member 320. An example of a conductive epoxy is Bisphenol epoxy resin with silver particulates to enable conductivity. The particulates may be from 70-90% of the resin composition. The resin may then be combined with a hardener (e.g., 100 parts resin per 6 parts hardener.) The conductive epoxy 312 is in electrical communication with the conductive medium 314 allowing for a conductive path from the conducting member 320 to the conductive medium 314. Accordingly, use of the conductive epoxy 312 secures the conducting member 320 to the assembly 302 while electrically coupling the conducting member 320 to the transducer via the conductive coating 314.

Although variations of the transducer assembly include a tip and housing, the invention may omit the transducer covering and other structures not necessary to generate a source signal and receive a reflected signal. Therefore, it is contemplated that the invention may simply have a transducer that is coupled to a controller.

When used in the devices 200 described herein, the tip 208 of the sensing assembly may comprise the transducer 308 shown above, or the coating 314. In alternative variations, the tip 208 of the sensing assembly may comprise a tip 304 that is affixed to the transducer assembly 302 and as shown in FIGS. 6A-6D.

FIGS. 6A-6D, illustrate possible variations of tips 304 for use with the transducer assembly. It is noted that these variations are provided for illustrative purposes and are not meant to be exhaustive. The tips 304 of the present invention may function simply as a blunting tip (but still passes and receives ultrasound signals) or as a lens to disperse and/or direct the signal over a substantial portion of the outer surface of the tip 304. When configured to function as a lens, the tip 304 is adapted to disperse and/or direct (e.g., by diffraction) a reflected signal towards the transducer (not shown in FIGS. 6A-6D). Accordingly, given the above described configuration, the inventive device 300 will be able to detect vessels with substantially most of the tip 304. The tip may comprise a signal directing means.

When configured to function as a lens, the tip 304 is designed such that it interferes and redirects the signals in a desired direction in a manner like a lens. It also may be desirable to place an epoxy between the tip 304 and the transducer. Preferably, the epoxy is thin and applied without air gaps, bubbles or pockets. Also, the density/hardness of the epoxy should provide for transmission of the signal while minimizing any effect or change to the source signal. The configuration of the transducer assembly 302 permits the lens tip 304 to disperse a signal over a substantial portion of its outer surface 244. The lens tip 304 also is adapted to refract a reflected signal towards the transducer 308. Accordingly, given the above described configuration, the inventive device will be able to detect vessels with any part or substantially the entire lens tip 304 that contacts tissue.

Although the tip of the present invention is able to transmit a source signal and receive a reflected signal, the invention is not limited to requiring both functions. For example, the inventive device could be configured to generate a source signal and direct the source signal to an area of interest but a second device or transducer assembly could be used to receive the reflected signal. Accordingly, a separate device could be used to generate the source signal with the inventive device being used to receive the reflected signal.

The tip 304 may be comprised of materials such as a dimethyl pentene, a methylpentene copolymer (plastic-TPX), aluminum, carbon aerogel, polycarbonate (e.g., Lexan), polystyrene, etc., or any other standard material used for ultrasound applications.

Figure 6A:
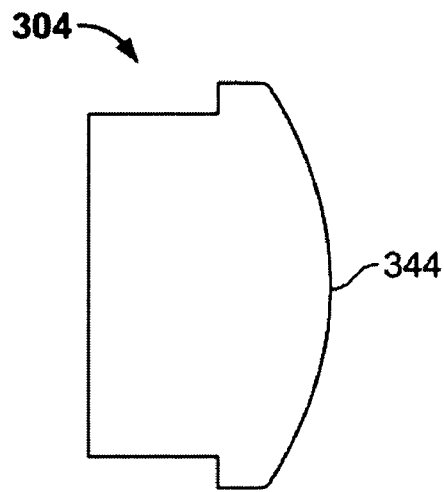
FIGS. 6A-6D, illustrate possible variations of optional sensing tips for use with the transducer assembly.
Figure 6B:
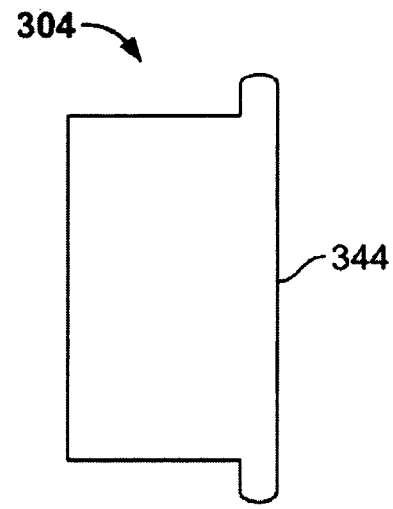
Figure 6C:
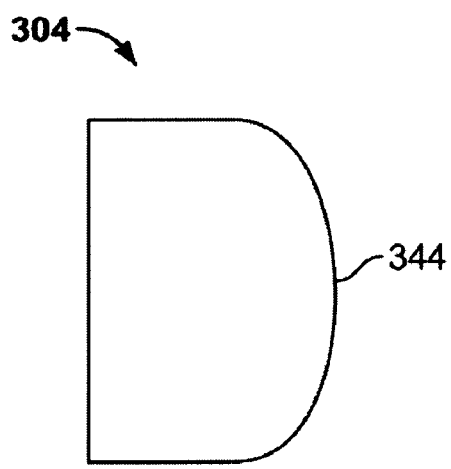
Figure 6D:
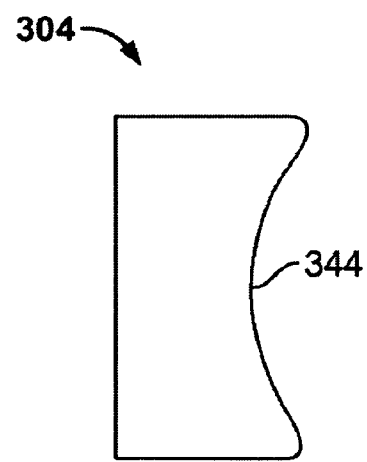

As illustrated in FIG. 6A, although the front surface 344 of the tip 302 is illustrated as being hemispherical, the tip 304 may have other profiles as well. For example, it is desirable that the tip 304 produce a certain amount of divergence of the signal being passed therethrough. However, depending on a variety of factors (e.g., material, frequency of the signal, etc.) a tip 304 may encounter excessive divergence which is destructive to the outgoing signal. Accordingly, it may be desirable to produce a tip 304 as illustrated in FIG. 6B in which a front surface 344 of the tip 304 is substantially flat. The degree of flatness of the tip 304 will often depend upon experimentation to reduce the amount of destructive reflections, thus minimizing excessive divergence due to differences in speed of sound in tip versus tissue. For example, when using a tip that is conducive to an ultrasound signal (e.g., TPX) a rounded tip can be used since there is not excessive divergence of the source signal. Use of a material that is not as conducive to ultrasound requires a flatter tip due to the resulting divergence of the source signal. FIG. 6C illustrates another variation of a tip 304 having a rounded front surface 344 but with no projections on the sides of the tip 304. FIG. 6D illustrates a tip 304 with a concave front surface 344.

In any case, the tip will be configured to avoid sharp edges that may cause any unintended damage to tissue while the device is being used to determine the presence or absence of a blood vessel. In such a case, for example, the tip may be designed such that it doesn't have sharp edges, or any sharp edges may be covered by other parts of the device (e.g., the elongate member, an outer sheath, etc.)

Commonly assigned patent publication nos. US20020128647A1; US20020138074A1; US20030130657A1, and US20050107783A1; disclose additional variations of transducer assemblies and modes of securing such assemblies to the device. The entirety of each of which is incorporated by reference herein.

Figure 7:
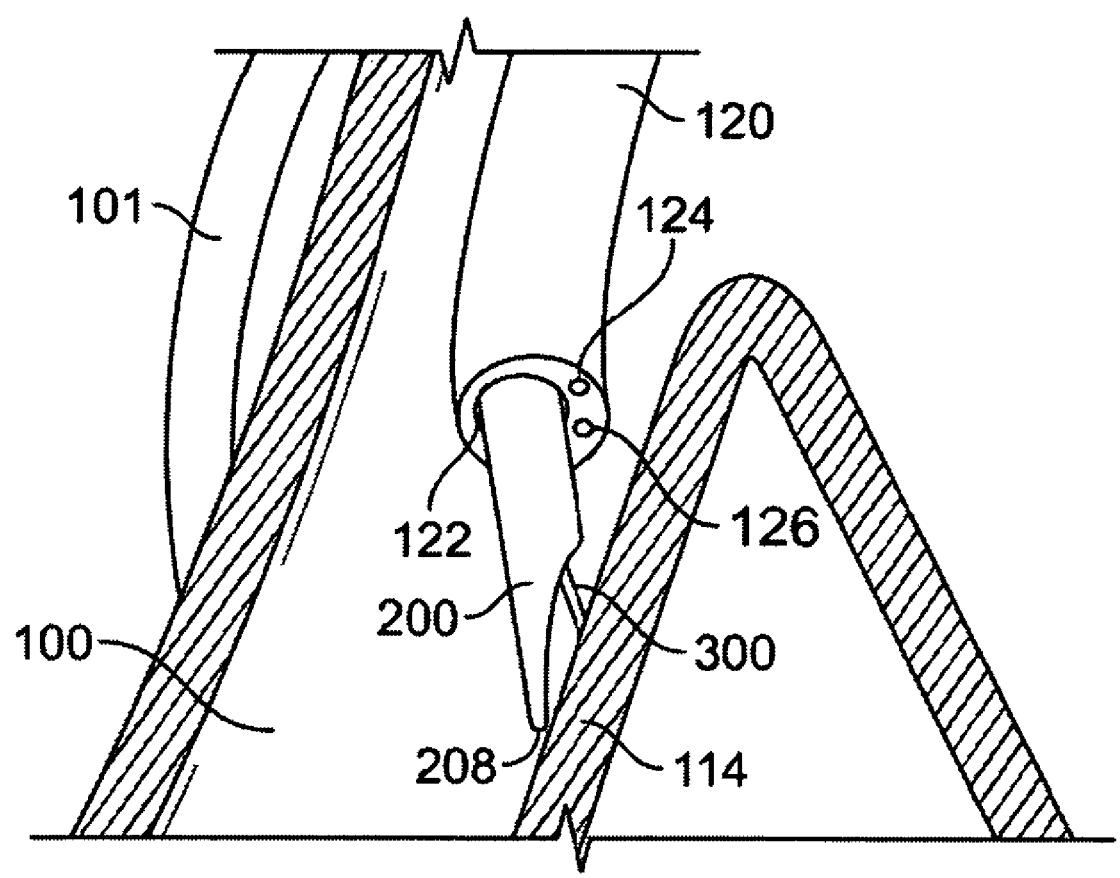
FIG. 7 illustrates an example of using the device to scan a target site prior to, during, and after performing a procedure at the target site.

FIG. 7 illustrates an example of use of the devices described herein. Although the figures show a single variation, it is contemplated that any variation of the device may be substituted. In the illustrated example, the device creates an extra-anatomic passage in the airway wall tissue within a lung. However, it is understood that the device may be used in any part of the body and for any application. For example, variations of the device may be used during a biopsy procedure to scan for blood vessels, and remove a biopsy sample within the tissue piercing member.

FIG. 7 shows an access device 120 advanced into the airways 100 of a lung. The access device 120 may be a bronchoscope, endoscope, endrotracheal tube with or without vision capability, or any type of delivery device. The access device 120 will have at least one lumen or working channel 122. In the illustrated version, access device 120 includes a light 124 and vision 126 capabilities. For example, location of the site may be accomplished visually, or with additional equipment such as a CT scan to locate areas for treatment. In cases where the access device 120 is a bronchoscope or similar device, the access device 120 is equipped so that the surgeon may observe the intended target site 114. In some cases it may be desirable for non-invasive imaging of the procedure. In such cases, the access device 120 as well as the other devices discussed herein, may be configured for detection by the particular non-invasive imaging technique such as fluoroscopy, "real-time" computed tomography scanning, or another technique being used.

FIG. 7 also illustrates advancement of a variation of the inventive device 200 through the channel 122 of the access device 120 towards the target site 114. The medical practitioner then uses the sensing element 208 to inspect the target site 114 to determine whether a blood vessel 101 is adjacent to the site. If a blood vessel is detected at or near the site 114, then another target site may be selected.

Once the practitioner determines that the site is free of any blood vessel 101, the practitioner may insert the medical appliance 300 (in this case a transbronchial aspiration needle) into the target site without removing the catheter 200 and sensing element 208 from the tissue. Accordingly, variations of the device require sufficient stiffness so that the tissue may be adequately probed without collapse of the sensing element 208 or the segment carrying the element. As described above, the system 150 provides the medical practitioner with audio or visual signals so that the practitioner can determine whether it is sufficiently safe to make an opening in the tissue.

A further variation of the invention may include configuring the transducer assembly and/or controller to have different levels of sensitivity. For example, a first level of sensitivity may be used to scan the surface of tissue. Then, after creation of the opening, the second level of sensitivity may be triggered. Such a feature acknowledges that scanning of tissue on, for example, the airway wall may require a different sensitivity than when scanning tissue within the parenchyma of the lung.

It should be noted that the invention includes kits containing the inventive device with any one or more of the following components, a Doppler ultrasound controller, a conduit delivery catheter and a radially expandable conduit detachably connected to the distal end of the delivery catheter, as described in one or more of the applications listed above, and a bronchoscope/endoscope.

In the above explanation of Figures, similar numerals may represent similar features for the different variations of the invention.

The invention herein is described by examples and a desired way of practicing the invention is described. However, the invention as claimed herein is not limited to that specific description in any manner. Equivalence to the description as hereinafter claimed is considered to be within the scope of protection of this patent.

Additionally, the devices of the present invention may be configured to locate a target site for creation of a collateral channel in the tissue and to create an opening in tissue. As discussed above, a benefit of this combination feature is that a single device is able to select a target location and then create an opening without having been moved. Although the device is discussed as being primarily used in the lungs, the device is not limited as such and it is contemplated that the invention has utility in other areas as well, specifically in applications in which blood vessels or other structures must be avoided while cutting or removing tissue (one such example is tumor removal).

The above illustrations are examples of the invention described herein. It is contemplated that combinations of aspects of specific embodiments/variations or combinations of the specific embodiments/variations themselves are within the scope of this disclosure.

We claim:

1. A method for performing a tissue biopsy on a tumor in a lung comprising:

advancing a far end of a catheter into an airway within the lung and in the vicinity of the tumor where the catheter has a working channel and a Doppler ultrasound assembly that is affixed to the catheter and is offset from an axis of the working channel;

sensing for the absence of blood vessels along the airway using a Doppler ultrasound assembly associated with the far end of said catheter;

extending a working tip of a medical appliance from the working channel at said far end of said catheter, through a wall of said airway, and into said tumor such that catheter does not obscure the Doppler ultrasound assembly; and removing a tissue sample from said tumor with said appliance.

2. The method of claim 1 where said medical appliance is a biopsy coring device.

3. The method of claim 1 further comprising the step of advancing a bronchoscope into the airway, and advancing said catheter through a lumen in said bronchoscope.

4. The method of claim 1 where the far end of the catheter comprises a distal opening for said working tip of said medical appliance to exit, and wherein said opening is beveled.

5. The method of claim 1 wherein said Doppler ultrasound assembly is positioned distal to said distal opening.

6. The method of claim 1 further comprising identifying a location that is free of a blood vessel during sensing and holding the Doppler ultrasound assembly against the location while simultaneously extending the working tip into said tumor.

* * * * *